United States Patent [19]

Kung et al.

[11] Patent Number: 4,888,011
[45] Date of Patent: Dec. 19, 1989

[54] ARTIFICIAL HEART

[75] Inventors: Robert T. V. Kung, Andover; Param I. Singh, Lexington, both of Mass.

[73] Assignee: Abiomed, Inc., Danvers, Mass.

[21] Appl. No.: 216,028

[22] Filed: Jul. 7, 1988

[51] Int. Cl.[4] .................................................. A61F 2/22
[52] U.S. Cl. .......................................... 623/3; 600/16
[58] Field of Search ...................... 623/3; 600/16, 17; 417/393

[56] References Cited

U.S. PATENT DOCUMENTS

| | | | |
|---|---|---|---|
| 3,434,162 | 3/1969 | Wolfe | 623/3 |
| 4,555,222 | 11/1985 | Casilli | 417/393 |
| 4,687,424 | 8/1987 | Heimes | 623/3 |
| 4,820,300 | 4/1989 | Pierce | 623/3 |

Primary Examiner—Richard J. Apley
Assistant Examiner—Stephanie L. Iantorno
Attorney, Agent, or Firm—Lahive & Cockfield

[57] ABSTRACT

An artificial heart system employing left and right pumping chambers each divided by a membrane into a blood pumping chamber and a hydraulic pumping chamber and a hydraulic pumping system for alternately pumping hydraulic fluid from said left hydraulic chamber toward said right hydraulic chamber and vice versa. A balancing chamber including a flexible membrane placed in the left atrium so that the membrane changes position with changes in the patient's blood pressure, the hydraulic portion of said balancing chamber being fluidically coupled to the right hydraulic pumping chamber in order to allow for a different pumping volume between the left blood pumping chamber and the right blood pumping chamber. A control system employing an algorithm to control the speed of the hydraulic pumping and the direction of flow of the hydraulic pumping in response to sensors sensing the left atrial pressure and the completeness of stroke of the left blood pumping chamber.

7 Claims, 5 Drawing Sheets

ARTIFICIAL HEART

BACKGROUND OF THE INVENTION

This invention relates in general to artificial hearts and more particularly to an artificial heart system that will respond to varying physiological demand and includes mechanisms accommodating the actual flow imbalance between pulmonary and systemic circulations.

Over the last several years progress in developing a permanent artificial heart for implantation in a patient as a substitute for a failed natural heart has been steady. Initial clinical application of total artificial heart as a bridge to transplantation was done in 1969. This has been followed by several additional cases at various institutions. In 1982 the first pneumatically driven tethered artificial heart intended for permanent replacement was implanted. Among the issues that need to be addressed in an untethered artificial heart system are control strategies that respond to varying physiological demand, and mechanisms for accommodating the natural flow imbalance between the pulmonary and systemic circulations. The left-right cardiac output differences have been well established. Normally this difference appears to be ten to fifteen percent with the left side flow always greater than the right side flow. Artificial heart systems must account for this inherent physiological characteristic.

For externally actuated pneumatic systems the external drive system can be set to accommodate this flow difference. In permanent systems, however, this flow difference compensation has to be considered in conjunction with the system compliance and control. In the prior art two approaches, control valve regurgitation and a gas compliance chamber have been used in experimental systems. In particular a controlled outflow valve regurgitation in the artificial right heart has been employed. (Lioi, A. P.; Kolff, W. D.; Olsen, D. B.; Crump, K.; Isaacson, M. S.; and Nielson, S. D.; "Physiological Control of Electric Total Artificial Hearts", in *Devices and Contractors Branch Contractors Meeting* 1985, Program and Abstracts, Dec. 1985, 89.) In this approach the left and right sides of the heart are pumped alternately by a reversing hydraulic pump. A deliberate outflow leakage designed into the right pump is intended to accommodate the flow difference and obviate the need for a compensating chamber. However the regurgitant flow is only a function of the square root of the difference between the pulmonary diastolic pressure and the right atrial pressure. This results in a near constant compensating flow which may well be inadequate to accommodate time varying flow differences. Also, changes in the orifice size over the long duration can cause this flow imbalance to drift from the preset value.

A second prior art approach has employed a gas compliance chamber (with its problems of gas composition and pressure changes) and passive filling to accommodate the flow difference in conjunction with a stroke-time division scheme. (Rosenberg, G.; Snyder, J.; Landis, D. L.; Geselowitz, D. B.; Donachy, J. H.; and Pierce, W. S., "An Electric Motor-Driven Total Artificial Heart: Seven Months Survival In The Calf", Trans Am Soc Artif Intern Organ, 15, 69, 1984.)

In addition to the left-right balance problem, the prior art has actively worked on a control system for controlling the artificial heart. Externally actuated pneumatic systems have commonly been operated under preset drive parameters: drive pressure, vent pressure, beat rate, and systolic/diastolic ratio.

SUMMARY OF THE INVENTION

It is therefore an object of this invention to provide an artificial heart which is an alternately left-right pumping device in which the basic control strategy is to adjust hydraulic fluid flow and beat rate on a beat-by-beat basis so that the device is stable and sensitive to both left and right atrial pressures.

It is a further object of this invention to provide for the left-right blood flow imbalance by incorporating in a hydraulically pumped system, a hydraulic imbalance chamber positioned to respond physiologically through the blood flows in the right and left side of the heart to maintain an appropriate imbalance.

Broadly speaking, the present invention utilizes an alternately left-right pumping device with the left and right pumping chambers, each including a membrane or diaphragm separating the chamber into a blood flow section and a hydraulic section. During left-side blood pump ejection, hydraulic fluid is being pumped from the right hydraulic section through a hydraulic pump into the left hydraulic section, resulting in concurrent filling of the right side blood pump while left side ejection is taking place. The hydraulic flow is reversed for right side ejection and left side filling.

A third hydraulic chamber small in volume compared to the left side hydraulic section and right side hydraulic section of the blood pumping chambers and having fluid communication with the right side hydraulic section is preferably incorporated on the proximal (atrial) side of the left pump inflow valve and includes its own flexible diaphragm in contact with blood inflow through the left pump. This third chamber serves to maintain the natural imbalance in the left and right side flows by changing the right hydraulic section fluid volume during a beat. Without this additional balancing hydraulic section, the left and right blood pumping chambers would always provide equal stroke volumes. With the incorporation of this additional hydraulic balance chamber, the volume pumped by the right side pump is reduced by the balancing chamber. The distribution of hydraulic fluid between the right side chamber volume and the balancing chamber volume is altered dynamically by the physiological pressure in the pulmonary artery and in the left atrium, thus adjusting the volume pumped by the right side fluid flow chamber on a beat-by-beat basis. The flow resistance between the hydraulic section on the right side chamber and the hydraulic balancing chamber is designed to maintain the overall natural flow imbalance.

The balancing chamber is placed in the left atrial inflow to provide a negative feedback on the right chamber fluid volume. A high left atrial pressure, indicating too much flow from the right side, will decrease the hydraulic volume in the balancing chamber and increase the hydraulic volume in the right side chamber. The result is to reduce the flow on the right side. Conversely, a low left atrial pressure will increase the right side flow. This provides a stable feedback to maintain the desired right side flow relative to the left side flow.

The primary factor is that the membrane of the balancing factor be in contact with blood flow somewhere in the system or in the patient's connecting atria or arteries so that a variation in blood pressure will produce a positioned change in the membrane. While the left atrium is the preferred site for this balancing chamber, other suitable sites include distal to the right side outflow valve, or right atrial inflow.

An electrohydraulic energy system drives the blood pumps employing a hydraulic fluid, typically methyl silicone, operating at physiological pressures. This hydraulic coupling between the blood pumps and the energy converter allows geometric flexibility. There is a 1:1 correspondence between blood and hydraulic fluid displacement. The hydraulic fluid and blood are immiscible with negligible fluid transfer across the interface. The energy converter consists of an unidirectional axial pump driven by a brushless d.c. motor with flow reversal accomplished by a two-position, sliding sleeve valve. There are, then, essentially two moving parts, the pump motor and one of the valving sleeves. The motor sits immersed in the hydraulic fluid which fills the energy system housing. This ensures temperature uniformity of the system. Waste heat is transferred to the blood across the pump diaphragms and from the housing to contacting body fluid and surfaces.

A simple two-level control strategy results in a system responsive to physiological demands. Sensors in the hydraulic fluid are indicators of the atrial filling pressures. Other sensors detect full stroke of the left blood pumps. Thus there are two inputs and they control two outputs: motor speed or rate of filling/ejection, and beat rate. In this system the systolic/diastolic ratio is held constant. The rate of ejection is incrementally increased for a given beat rate until the pump is ejecting completely. If, in addition to complete ejection full stroke is achieved, then the beat rate is increased. The reverse occurs if fill volumes are too low. The strategy is independent of outflow impedances. The artificial heart system reacts (both stroke volume and beat rate) to changes in the available fill volume and adjusts the outflow pressure to accommodate the outflow impedance. Similarly since each pump is filled by active withdrawal of hydraulic flow, fill characteristics are not determined by mechanical impedances, but can be tailored to a desired characteristic.

DESCRIPTION OF THE DRAWING

In the drawing:

FIG. 4b is an illustration in top view of the embodiment of FIG. 4a;

DETAILED DESCRIPTION OF THE INVENTION

Figure 1:
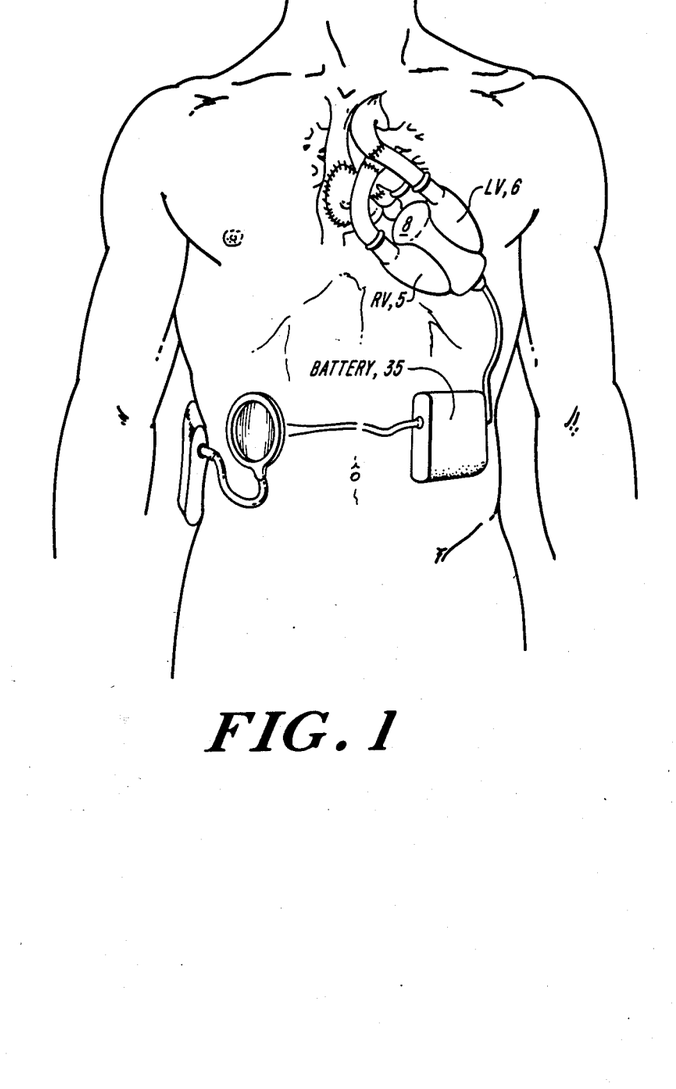
FIG. 1 is an illustration generally in perspective view of an artificial heart constructed in accordance with the principles of this invention placed orthotopically in the thoracic space.

The Figures generally illustrate a preferred embodiment of the artificial heart system of this invention. In FIG. 1 the anatomical placement of the system components is illustrated. The system is intended to replace the ventricles of the natural heart and is inserted within the thoracic cavity in place of the natural heart and coupled to the natural heart right and left atria and also to the pulmonary artery and the aorta. The cylindrical energy converter 8 and the blood pumps 5 and 6 approximate the shape and volume of the natural heart and are implanted in the pericardial volume vacated by the excised natural heart. The blood pumps 5 and 6 are seamless with no steps or connectors from proximal to the inflow valve through to the outflow graft distal to the outflow valve. The valves (not shown) are trileaflet valves placed at the flow inputs and outputs of each of the ventricles. The internal blood pump surfaces including the integral trileaflet valves are fabricated from a non-toxic, non-mutagenic polyetherurethane material made by Abiomed, Inc., Danvers, Mass. under the trademark Angioflex.

Figure 2:
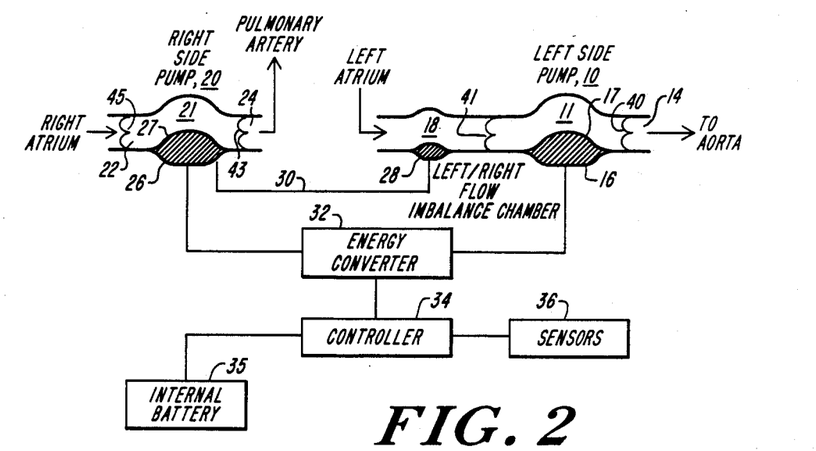
FIG. 2 is an illustration generally in diagrammatic form of one embodiment of an artificial heart system constructed in accordance with the principles of this invention.

A block diagram of an artificial heart system in accordance with the principles of this invention is illustrated in FIG. 2. The two blood pumps 10 and 20, each with a stroke volume typically of 85cc, are connected to the energy converter 32, which includes both a fluid switch and a hydraulic pump. As illustrated in FIG. 2 the left side pump 10 includes a blood flow pumping chamber 11 having a blood input section 18 from the left atrium and a blood output port 14 to the aorta. Trileaflet valves 40 and 41 have the normal valving function for the blood flow from the pump volume 11. The pump 10 also includes a hydraulic pumping section 16 which is fluidically coupled to the hydraulic pump 32. The right side pump 20 is similarly constructed and is coupled between the right atrium at its blood input port 22 and the pulmonary artery at its blood output port 24. This pump also includes a hydraulic pumping section 26 fluidically coupled to the energy converter 32.

In addition to the parts described the left pump 10 includes at input cuff 18 a hydraulic section 28 which is fluidically coupled through conduit 30 to the right side hydraulic section 26. The volume of hydraulic section 28 is small compared to the volume of hydraulic sections 16 and 26 (typically a 1:5 ratio).

Figure 9A:
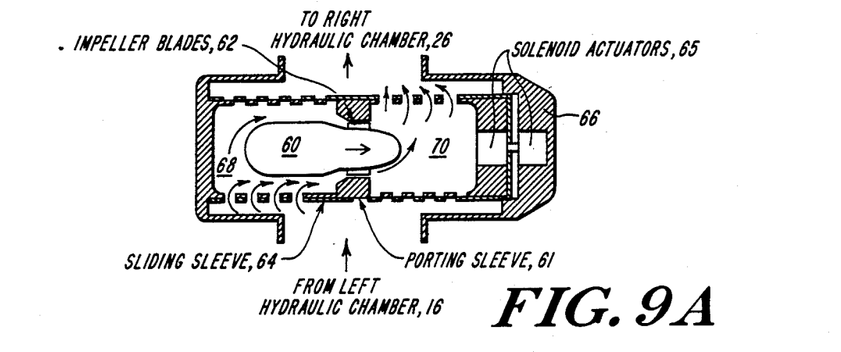
FIGS. 9a and 9b are illustrations in cross sectional view of an energy converter suitable for use in the embodiment of FIG. 2.
Figure 9B:
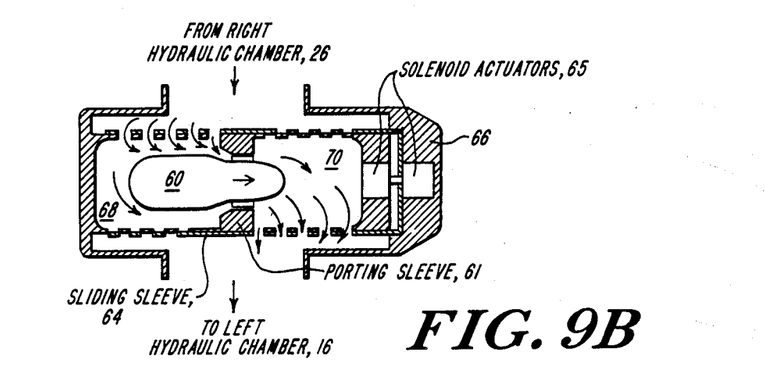

The energy converter 32 includes a hydraulic pump which is coupled through a fluid switch to the sections 16 and 26. The fluid switch and hydraulic pump in energy converter 32 are controlled by a controller 34 which receives electrical power from internal battery 35 and an external battery (not shown) and control signals from sensors 36. The converter is more completely described in conjunction with FIG. 9, but provides for an axial flow pump with a sleeve valve which can be electrically switched. Depending upon the position of the sleeve valve, fluid is pumped either in the direction away from hydraulic section 16 and toward hydraulic section 26 or in the other position, away from hydraulic section 26 and toward hydraulic section 16. The controller 34 controls the position of this switch in accordance with the response to its program and input signals from the sensors 36.

The pump cycle is as follows. During left side systole, blood is being ejected from the left blood chamber 11 into the aorta. Concurrently the right side blood chamber 21 is being filled from the right atrium. If the blood volume filling the right pump from the right atrium is less than the volume ejected from the left side blood chamber the compensating chamber 28 adjusts the compensating chamber volume formed in the cuff 18 to accommodate this volume difference by virtue of hydraulic fluid flowing from the compensating hydraulic chamber 28 into the right hydraulic section 26. The resultant volume change in the balance chamber in cuff 18 is naturally compensated for by the compliant left atrium during its filling phase. During right side ejection and left pump filling, the process is reversed, and the blood volume displaced by the compensating chamber 18 in the left atrium is transferred into the left side of the blood chamber 11 in addition to the remainder of the blood volume in the left atrium. This has the added advantage of aiding left atrial filling during left pump systole and left pump filling during left pump diastole. As will be described in more detail below the flow resistance of the hydraulic conduit 30 is selected to maintain the necessary natural left-right flow imbalance.

The advantages of this compensation technique are:
(1) its sensitivity to physiological pressure changes, thus providing stable feedback, and its insensitivity to valve performance changes,
(2) no tissue encapsulation or gas composition changes on the moving diaphragm as would be the case of a gas compliance bag, and
(3) simple integration into the left side inflow cuff of the compensating device.

The basic control philosophy, implemented on a beat-by-beat basis, is to pump as much blood volume as is available in the atria. This can be achieved by first controlling the hydraulic motor speed to pump the available blood volume at a fixed beat rate. When the available atrial volume exceeds the pump stroke volume, the beat rate is increased. Similarly, in a fill limited situation, the motor speed and the beat rate are reduced to avoid overpumping. The motor speeds are controlled by pressure sensing, while the beat rate is controlled by stroke volume sensing. The atrial pressures govern the motor speeds during the respective fill cycles. By indirectly sensing the pressure in the atrium (by placing the pressure sensors in the hydraulic section 16 and 26), the motor speed is adjusted to insure that the end diastolic atrial pressure is near zero at the end of a fill cycle. The flexible bladder 17 separating blood and hydraulic fluid is tension-free during fill and ejection, and pressure sensors in the hydraulic chambers reflect the atrial pressures. At the end of filling, the bladder rests on a base plate, thus decoupling the hydraulic and the blood pressures.

A second parameter which indicates the current stroke volume is used to determine the beat rate of the artificial heart. The control for the beat rate is as follows: when the left pump 10 indicates a full stroke, the beat rate is increased, otherwise the beat rate is decreased.

For blood pumps of 85 cc volume, a compensation volume of 13 cc will accommodate up to 15% difference between the left and the right side flows. The compensating hydraulic volume 28 communicates with the right hydraulic section 26. At the initiation of right side filling, the right hydraulic chamber section 26 has 85 cc of fluid and the compensation volume 28 has 13 cc of fluid. At the end of filling, the right side blood chamber 21 can contain 72 to 85 cc of blood depending upon how many cubic centimeters of fluid in the compensating volume 28 have transferred to the hydraulic chamber 26. This determines the stroke volume, provided that at the end of right pump ejection the compensation volume 28 is replenished and readied for the next cycle. The hydraulic flow (Fc) in and out of this compensation volume 28 is governed by the following equation, $$F_c = (P_H - P_b)/R$$

where $P_H$ is the hydraulic pressure in the right chamber 26 and $P_b$ is the blood pressure in cuff 18 in contact with the flexing bladder of the compensation volume, and R is the fluidic resistance of the conduit 30 connecting the two chambers. For $F_c < 0$, fluid is flowing into the right hydraulic chamber 26. To insure a full compensation chamber prior to right side filling, $|F_c|_S > |F_c|_D$, that is the filling rate of the chamber should be greater than its draining rate. (The subscripts S and D denote right side systole and diastole respectively.)

Under these physiological circumstances, $|F_c|_S > |F_c|_D$. More importantly, $|F_c|_D$ is sensitive to the left atrial pressure. A high left atrium pressure, indicative of high right side flows, results in higher $|F_c|_D$, which in turn reduces the right side flow. This negative feedback is very desirable for stable operation.

In order to maintain a mean flow difference of 7.5% at a left atrium pressure of 7.5 mmHg and a median beat of 80 BPM, the required flow resistance, R, is given by $$R = \Delta P/Q = (8\mu L)/(\pi r^4)$$

where $\mu$ = viscosity of silicone fluid = 0.01 poise
L = length of the connecting conduit
r = radius of the conduit.
Q at 80 BPM, 50% diastole, and 7.5% flow difference (6.5 cc/per beat) is approximately 17.3 cc/sec. Thus R = 0.43 mmHg/cc/sec, for L = 3 cm, and $P_b$ = 7.5 mmHg, R is 0.11 cm. Thus a 0.22 cm diameter conduit, 3 cm in length, can maintain a flow difference of 7.5%. At left atrium pressure of 15 mmHg, 15% flow difference can be maintained.

The time constant for this feedback depends on R and the pulmonary venous compliance (c). Using a compliance of 6.5 cc/mmHg, the response time of this feedback mechanism is = RC = 2.8 sec. Thus changes in the right side flow that deviates from the "normal" requirement can be compensated for rapidly.

The design criteria for this balance compensation chamber are: (1) the hydraulic fluid volume must be limited to and not exceed the desired value, and 2) the diaphragm in contact with blood must be free of any supporting structures on the blood-facing side. An annular baseplate sandwiched between two flexible diaphragms will satisfy these criteria.

The atrial pressure sensors are placed within the hydraulic section 16 and 26 and, because the hydraulic pressure is in equilibrium with the pressure of the blood in the chambers, these provide for accurate reading of the atrial fill pressure during fill. The stroke sensors are devices which measure the position of the diaphragm 17 which forms the interface between the flow volume and the hydraulic section in the left blood pump, as indicative of whether there is a full stroke.

Figure 3A:
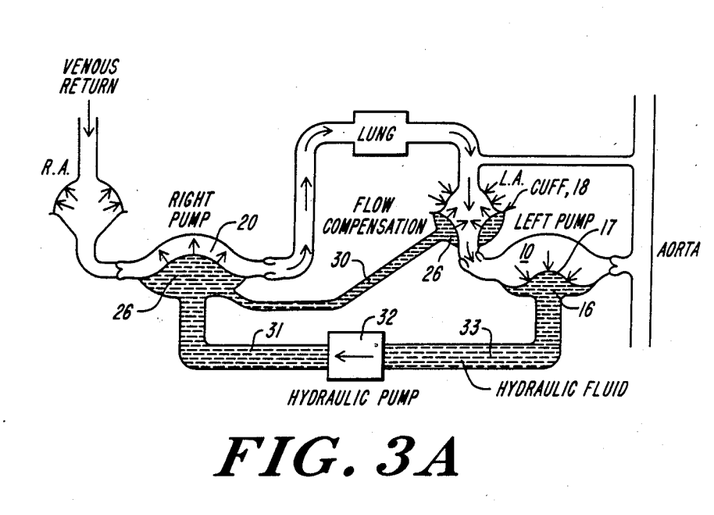
FIGS. 3a and 3b are a diagrammatic illustration of the operation of the embodiment of FIG. 2.

FIG. 3a illustrates the operation of this system when the right pump 20 is pumping by virtue of the hydraulic pump forcing hydraulic fluid into the hydraulic section 26, while the left pump is filling with blood returned from the lung under the influence of the membrane 17 withdrawing as the hydraulic fluid is pumped from the left hydraulic section toward the right.

Figure 3B:
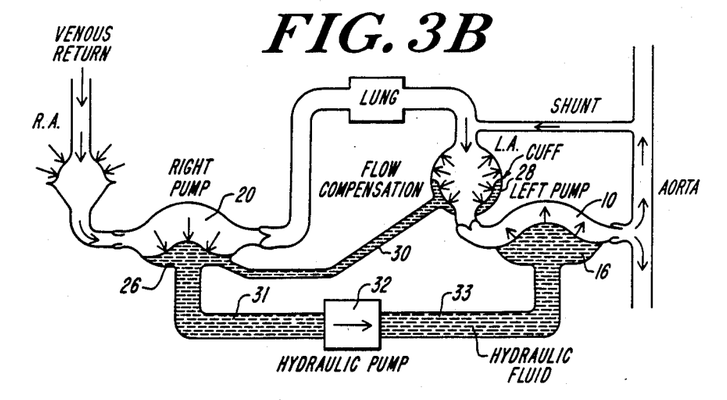

FIG. 3b is the opposite configuration, in which the left pump is ejecting blood into the aorta under the influence of hydraulic fluid pumped from the right pump section 26 into the left pump section 16, once again aiding the right pump chamber 20 in filling. At the same time the amount of hydraulic fluid in the flow balance compensation chamber 26 is determined by the pressure in the left atrium due to return blood flow.

Figure 4A:
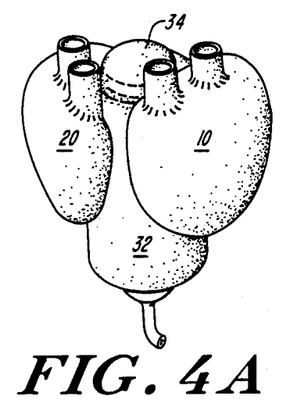
FIG. 4a is an illustration in perspective view of the artificial heart embodiment of FIG. 2.
Figure 4B:
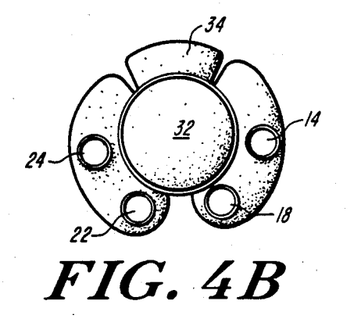

In FIG. 4a and 4b there is illustrated the physical configuration of the pumping chambers together with the energy converter showing the location of the inflow and outflow ports.

Figure 5:
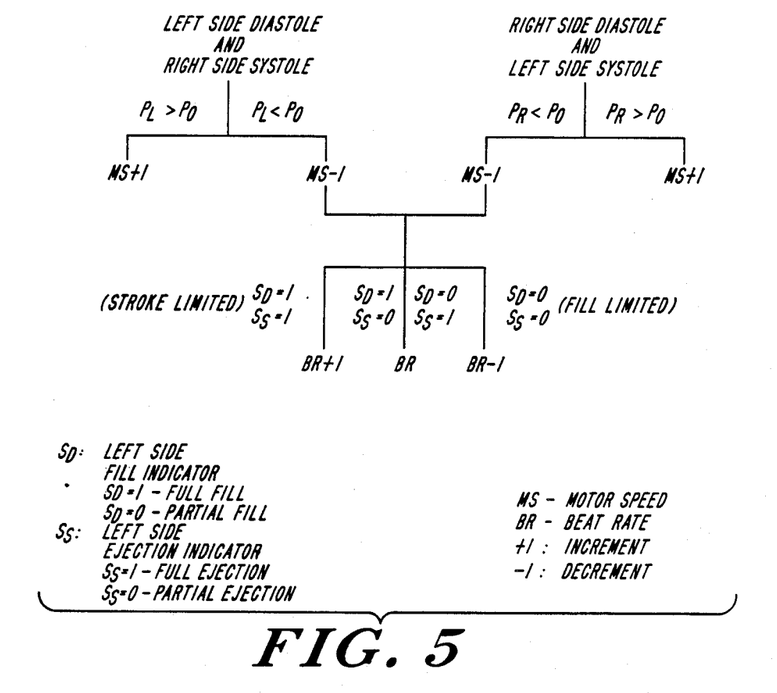
FIG. 5 is a diagram of an algorithm hierarchy for the control system of the artificial heart embodiment of FIG. 1.

The complete control algorithm decision tree is illustrated in FIG. 5. The control hierarchy is first fill governed (pressure sensing) followed by beat rate adjustment (full stroke indicator). Addressing first the left side diastolic phase, if the end diastolic pressure in the left chamber ($P_L$ is greater than some preset level ($P_o$) indicating that there is blood remaining in the left atrium, the motor speed during left side diastole and right side systole is incremented such that during the next beat the flow rate is increased to insure faster filling. Conversely, for $P_L < P_o$, overpumping is indicated and the motor speed is decremented. However, two situations can be encountered. In one case, if the left atrial blood volume is less than the blood pump stroke volume (fill limited), and complete filling did not occur (derived from the stroke indicator $S_D = 0$), and if during the subsequent left side systole only partial ejection ($S_s = 0$) occurred (right-side fill limited), the beat rate will be decremented. The second case occurs when the bladder bottoms on the hydraulic baseplate (full fill condition). Since the pressure is measured in the hydraulic chamber, $P_L$ will be less than $P_o$. The left stroke indicator will show a full bladder starting position ($S_D = 1$) prior to ejection. During the subsequent left side systole, if the left stroke indicator shows full ejection ($S_S = 1$), the beat rate will be incremented. The beat rate remains unchanged when neither of the above conditions occur.

Similarly, during right side filling (left side ejection), the hydraulic pressure in the right chamber is sensed to determine the right motor speed for the next beat. Beat rate changes occur only when both sides are fill limited ($S_D = 0$; $S_s = 0$) or when both sides are volume-limited by the prosthetic ventricles ($S_D = 3$); ($S_s = 1$).

This control mechanism, coupled with the flow-pressure characteristics of the axial flow pump, can automatically accommodate aortic and pulmonary pressure variations. For example, if the aortic pressure increases while the right side fill pressure remains unchanged, the motor speed for this half of the cycle will increase during the next beat to yield similar flow but at a higher aortic pressure. This algorithm does not assume that the peripheral resistance varies inversely with the cardiac output. It is well known that both arterial pressure and cardiac output can increase during exercise. This control mechanism does not assume any specific relationship between arterial pressure and vascular resistance. Up to the system performance limit, the device will adjust to variations in both the arterial pressure and the vascular resistance.

Figure 6:
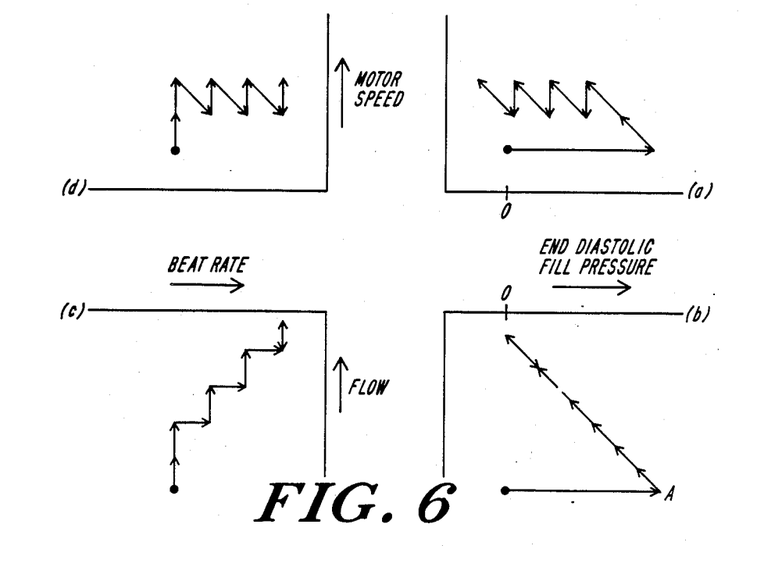
FIG. 6 is an illustration in diagrammatic form of the interrelationships of the sensed parameters and the control parameters, together with the resultant physiological parameter of the artificial heart embodiment of FIG. 2.

FIG. 6 shows interrelated plots of parameter changes on a beat-by-beat basis. Adjacent plots share common axes. This plot allows fill pressure, flow, motor speeds (left and right) and beat rate to be intercorrelated and illustrates the behavior of the parameters through a transition from a fill limited case to a stroke volume limited situation. The motor speed immediately increases due to the high filling pressure. Concurrently, the end diastolic pressure decreases and the flow increases. If after the 2nd increment, the pump is at full stroke, the beat rate will increment by one unit every other beat to maintain full stroke. This is accompanied by a further increase in the flow and decrease in the end diastolic pressure, while the motor speed decrements and increments on alternate beats. If after another six beats, the end diastolic pressure is negative, the motor speed will again operate on a beat-by-beat crossing and recrossing the zero pressure boundary at constant beat rate as illustrated. During this transition, flow increases due to increase in both the motor speed and the beat rate.

Table I shows the conditions governing motor speed and beat rate changes in accordance with the logic set forth in the algorithm hierarchy illustrated in FIG. 5.

TABLE I

CONDITIONS GOVERNING MOTOR SPEED AND BEAT RATE CHANGES

| Control Parameters* | Left Side Filling Motor Speed | Right Side Filling Motor Speed | Beat Rate |
|---|---|---|---|
| $P_L > P_o$<br>$P_R > P_o$ | Increase | Increase | N.C |
| $P_L > P_o$<br>$P_R > P_o$ | Increase | Decrease | N.C. |
| $P_L > P_o$<br>$P_R > P_o$ | Decrease | Increase | N.C. |
| $P_L < P_o$<br>$P_R < P_o$ | Decrease | Decrease | |
| $\begin{pmatrix} S_D = 1 \\ S_S = 1 \end{pmatrix}$ | | | Increase |
| $\begin{pmatrix} S_D = 0 \\ S_S = 0 \end{pmatrix}$ | | | Decrease |
| $\begin{pmatrix} S_D = 1 \\ S_S = 0 \end{pmatrix}$ | | | N.C. |
| $\begin{pmatrix} S_D = 0 \\ S_S = 1 \end{pmatrix}$ | | | N.C. |

*$P_L$—Left ventricular end diastolic pressure
$P_R$—Right ventricular end diastolic pressure
$P_o$—Reference pressure
$S_D$—Left side fill indicator; $S_D = 1$ is full fill; $S_D = 0$ is partial fill.
$S_S$—Left side ejection indicator; $S_S = 1$ is full ejection; $S_S = 0$ is partial ejection.

Figure 7:
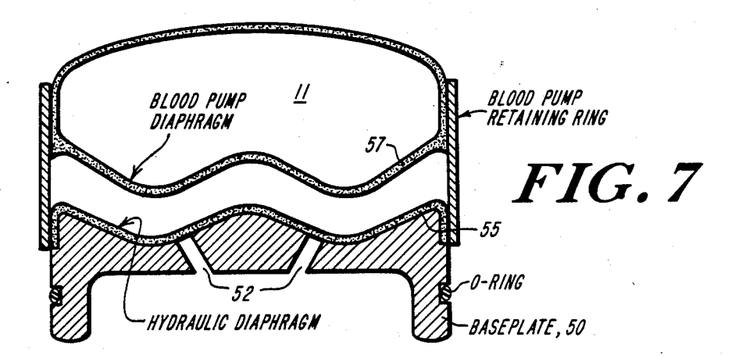
FIG. 7 is an illustration generally in cross sectional view of a detachable blood pump construction suitable for employment in the embodiment of FIG. 2.

In FIG. 7 there is illustrated in cross sectional view a suitable configuration of a pumping chamber existing in the art. The baseplate 50 has passages 52 therein to permit flow of the hydraulic fluid against the first diaphragm 55. In operation the base plate 50 is snapped over a base plate on the energy converter to allow the converter to provide for the flow of hydraulic fluid to extend the diaphragm 55 during systole of the chamber. An upper pump diaphragm 57 defines the flexible boundary of chamber 11. The sealed space (exaggerated for illustration purposes) between the hydraulic diaphragm 55 and the blood pump diaphragm 57 is lubricated with hydraulic fluid and thus the change of position of the hydraulic diaphragm 55 under the influence of hydraulic pressure pump in the converter 32 results in a corresponding displacement of the blood pump diaphragm 57.

The materials used in a circulatory system must be durable and biocompatible. The tissue contacting the materials must be non-mutagenic and non-toxic. In addition the blood contacting materials must be hemocompatible. The materials used for fabricating the pump diaphragms as illustrated in FIG. 7 at 55 and 57, must retain their hemocompatibility and mechanical integrity under the mechanical stresses. Suitable biocompatible materials are medical grade silicones, epoxy, titanium, glass fiber reenforced, epoxy composite, and polyetherurethane, made by Abiomed, Inc. of Danvers, Mass. under the trademark Angioflex.

Figure 8:
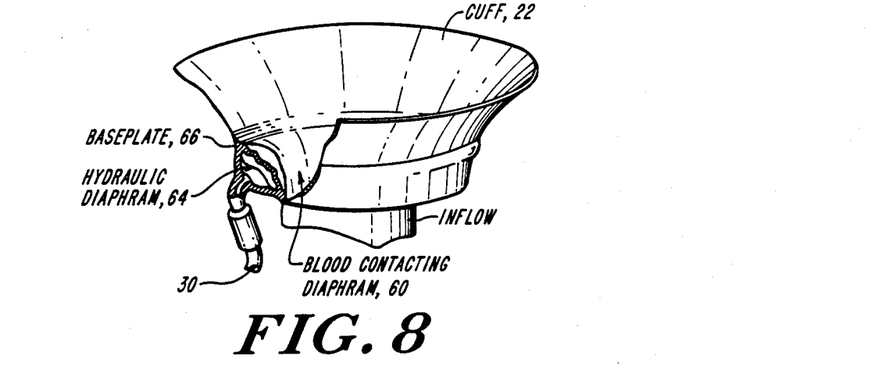
FIG. 8 is an illustration generally in perspective view and partially broken away to show a balancing chamber construction suitable for use in the embodiment of FIG. 2.

FIG. 8 is a view of the left inflow cuff 22 containing the imbalance compensation chamber. As shown, the compensation chamber contains a blood contacting diaphragm 60, a hydraulic diaphragm 64 and annular base plate 66 sandwiched between the two diaphgrams.

FIGS. 9a and 9b illustrate the energy converter in cross sectional view. FIG. 9a shows the converter in condition to pump hydraulic fluid from the left hydraulic chamber 16 to the right hydraulic chamber 26, while FIG. 9b shows the converter in condition to pump hydraulic fluid from the right hydraulic chamber 26 to the left hydraulic chamber 16. The converter consists of a unidirectional axial pump 60 having impeller blades to drive fluid from the left chamber 68 into the right chamber 70. The direction of outflow from the converter is controlled by the position of sliding sleeve 64 which can be moved axially in response to actuation of the solenoid actuators 65. The pump element 60 is fitted into a porting sleeve 61, which has slots on both sides of chamber 70, as well as slots on both sides of chamber 68. The sliding sleeve 64 is formed so that in one position, as shown in 9a, it blocks the slots in the lower portion of the outflow chamber 70 while opening the lower slots in the inflow chamber 68. The sleeve also, in this position, blocks the inflow chamber 68 slots in the upper portion of chamber 68 while opening the outflow slots in the upper portion of chamber 70. In its other position, shown in FIG. 9b, the exact opposite situation occurs. This arrangement provides for the hydraulic fluid to move, as indicated by the arrows, in one direction when the sliding sleeve is positioned as in FIG. 9a and in the opposite direction when the sleeve is positioned as in 9b. Signals from the control circuit actuate the solenoid actuator 65 and thus control the switching of the direction of flow from the pump.

While a specific embodiment of the artificial heart has been described above, it will be understood that many of the elements can be substituted for by other conventional parts.

We claim:

1. An artificial heart for implantation in the circulatory system of a human body comprising,
   first and second pumping chambers, each formed of a generally rigid outer shell and including a flexible membrane dividing each chamber into two sections, one section being a blood flow section and the other being a hydraulic section;
   an inlet port and an outlet port included in each blood flow section, said inlet and outlet ports being fluidically coupled to said patient's circulatory system, each of said hydraulic sections having an inlet port;
   hydraulic pumping means having first and second states, said hydraulic pumping means being hydraulically coupled to the inlet ports of said first and said second chamber hydraulic sections, said hydraulic pumping means in said first state pumping hydraulic fluid in a direction toward said first chamber hydraulic section and away from said second chamber hydraulic section, and in said second state pumping hydraulic fluid away from said first chamber hydraulic section toward said second chamber hydraulic section;
   a flexible membrane forming a wall of a sealed compartment placed so that changes in pressure of blood in said circulatory system produce changes in position of said membrane such that the volume of said compartment decreases with increase in blood pressure and increases with decreases in blood pressure, said sealed compartment being substantially smaller in volume than the hydraulic sections of said pumping chambers and having a hydraulic inlet port, hydraulic coupling means continuously fluidically coupled between said sealed compartment and the input port of said second pumping chamber hydraulic section; and
   control means connected to said hydraulic pumping means for switching said hydraulic pumping means from said first state to said second state.

2. An artificial heart for implantation in a human circulatory system comprising,
   first and second pumping chambers, each formed of a generally rigid outer shell and including a flexible membrane dividing each chamber into two sections, one section being a blood flow section and the other being a hydraulic section;
   an inlet port and an outlet port included in each blood flow section, at least the inlet port of each pumping chamber having a connecting cuff attached thereto, each of said hydraulic sections having an inlet port;
   hydraulic pumping means having first and second states, said hydraulic pumping means being hydraulically coupled to the inlet ports of said first and said second chamber hydraulic sections, said hydraulic pumping means in said first state pumping hydraulic fluid in a direction toward said first chamber hydraulic section and away from said second chamber hydraulic section, and in said second state pumping hydraulic fluid away from said first chamber hydraulic section toward said second chamber hydraulic section;
   a flexible membrane attached to the inner wall of the inlet cuff of said first pumping chamber forming a sealed hydraulic compartment therein, said flexible membrane being positioned to contact blood flow through the inlet of said first pumping chamber such that an increase in blood pressure in said inlet decreases the volume of said hydraulic compartment and a decrease in said blood pressure increases said volume, said sealed hydraulic compartment being substantially smaller in volume than the hydraulic sections of said pumping chambers and having a hydraulic inlet port, hydraulic coupling means continuously fluidically coupled between said sealed compartment and the input port of said second pumping chamber hydraulic section; and control means connected to said hydraulic pumping means for switching said hydraulic pumping means from said first state to said second state.

3. An artificial heart in accordance with either of claims 1 or 2 and including pressure sensors for sensing the atrial pressure at each of said pumping chambers, and further including stroke sensors for sensing whether said first chamber has achieved a full stroke, said sensors providing output signals to said control means to control the rate of flow of hydraulic fluid though said hydraulic pumping means, and to control the frequency at which said hydraulic pumping means switches from one state to the other.

4. An artificial heart in accordance with either of claims 1 or 2 wherein said pumping means includes a variable speed unidirectional hydraulic pump and switchable valving means to direct the flow from said pump in one direction when said valve is in one position and in the other direction when said valve is in a second position in response to signals from said control means.

5. An artificial heart in accordance with claim 3 wherein said pumping means includes a variable speed motor and wherein the signals from said sensors cause said control means to vary the speed of said motor according to a predetermined algorithm.

6. An artificial heart in accordance with claim 5 wherein said pumping means includes switchable valve means which provides in one position fluid flow from said first chamber toward said second chamber and in said second position fluid flow from said first chamber toward said second chamber.

7. An artificial heart in accordance with claim 5 wherein said algorithm provides that;

whenever the pressure sensor signal for the chamber from which hydraulic fluid is flowing exceeds a predetermined value, said control means causes said motor speed to increase, and whenever the pressure sensor signal from said chamber is less than a predetermined value said control means causes said motor speed to decrease; and whenever said motor speed is decreased and said stroke sensor indicates that full stroke is achieved, said control means increases the frequency of switching, and when said stroke sensor indicates that full stroke has not been achieved said switching frequency is decreased.

* * * * *

UNITED STATES PATENT AND TRADEMARK OFFICE
CERTIFICATE OF CORRECTION

PATENT NO. : 4,888,011

DATED : December 19, 1989

INVENTOR(S) : Robert T. V. Kung and Param I. Singh

It is certified that error appears in the above-identified patent and that said Letters Patent is hereby corrected as shown below:

Column 7, line 59 delete "$(S_D=3)$" and insert -- $(S_D=1)$ --.

Signed and Sealed this

Eighth Day of December, 1992

Attest:

DOUGLAS B. COMER

*Attesting Officer*  *Acting Commissioner of Patents and Trademarks*